(12) United States Patent
Carkner et al.

(10) Patent No.: US 7,850,624 B2
(45) Date of Patent: Dec. 14, 2010

(54) MUSCLE THICKNESS SENSOR

(76) Inventors: Steve Carkner, 107 Lockhart Avenue, Ottawa, Ontario (CA) K2A 3R4; Allison Oldfield, 803-7303 Campeau Druve, Kanata, Ontario (CA) K2K 3M1

(*) Notice: Subject to any disclaimer, the term of this patent is extended or adjusted under 35 U.S.C. 154(b) by 339 days.

(21) Appl. No.: 12/044,352

(22) Filed: Mar. 7, 2008

(65) Prior Publication Data

US 2009/0227903 A1    Sep. 10, 2009

(51) Int. Cl.
*A61B 5/103* (2006.01)
(52) U.S. Cl. ..................................... 600/587
(58) Field of Classification Search .......... 600/587–595
See application file for complete search history.

(56) References Cited

U.S. PATENT DOCUMENTS

| | | | |
|---|---|---|---|
| 2003/0187370 A1* | 10/2003 | Kodama | 600/591 |
| 2004/0116571 A1* | 6/2004 | Su et al. | 524/404 |
| 2006/0149168 A1* | 7/2006 | Czarnek | 600/591 |
| 2007/0213455 A1* | 9/2007 | Amarasekera et al. | 524/588 |

\* cited by examiner

*Primary Examiner*—Max Hindenburg
*Assistant Examiner*—Michael C Stout
(74) *Attorney, Agent, or Firm*—Gordon Thomson

(57) ABSTRACT

A muscle thickness sensor for measuring muscle thickness over a bone structure having a resilient frame placed over the muscle of interest and compressible material within the frame to sense muscle contractions. The compressible material is strain sensitive and generates a detectable signal when compressed due to muscle flexure. The sensor is able to differentiate between muscle contraction and muscle relaxation and is generally immune to signal noise caused by movement of bone structure and adjacent muscle groups.

10 Claims, 7 Drawing Sheets

Figure 2 - Prior Art

MUSCLE THICKNESS SENSOR

FIELD OF THE INVENTION

This invention relates to the field of medical devices and more particularly to the field of surgery and specifically to anatomical gauges, namely, a muscle thickness sensor.

BACKGROUND OF THE INVENTION

In medicine, it is often necessary to detect changes in muscle thickness during contraction of a muscle which overlies a bone structure. The muscle thickness during contraction is a measure of muscle strength and can indicate the efficacy of neuromuscular blocking drugs.

Devices exist which, when temporarily fixed to the skin above the muscle, non-invasively detect changes in muscle thickness using a variety of techniques. For example, accelerometers can be used to detect the acceleration of the muscle as it contracts. Microphones can be used to detect pressure waves created by contraction of the muscle. These measurements can be then related to changes in muscle thickness. These devices can be effective for large muscles (ex. quadricep muscles).

The accuracy of existing devices in detecting changes in muscle thickness decreases when smaller muscles are monitored. With smaller muscles (ex. muscles in the face or hands), accelerations are small and thus the acceleration of such muscles can be damped considerably by the overlying structures of skin and fat. In addition, such tiny accelerations are easily lost due to large acceleration signals caused by the movement of other muscles in the area or by external acceleration forces such as whole body movement, vibration of the floor, or even pulsatile movement caused by blood flow.

Microphones are more accurate than accelerometers when used for detection of small muscle movement. However, microphones usually require an air or liquid coupling to the body to ensure adequate signal strength. Maintaining an appropriate gap between the active structure of the microphone and the skin, as well as maintaining an adequate and repeatable air-seal is very difficult. Microphones can be made to work in this application, but the attachment becomes problematic and the signal output from such devices tends to change over time due to the sensitivity of the coupling media. Microphones also tend to have a rigid structure, thus the curvature of the contracting small muscle creates a large gap between the muscle and the flat surface of the rigid device, not seen with larger muscles. With smaller muscles, the microphone gives less accurate results during muscle contraction because the microphone simply rides on top of the muscle. A further disadvantage of microphones is their inability to recognize local movements and distant movements. Since bodily fluids and bone are such excellent conductors of sound and vibration, microphones will pickup a combination of local movement and these other, unwanted, vibrational and pressure signals. A final disadvantage of microphones is that they are fundamentally based on sound which has an oscillatory nature. Microphones are therefore unsuited to differentiate between a muscle that is contracting and a muscle that is relaxing as they will both have similar sounds.

When considering the case where muscle overlies a bone structure, further complications exist. The bones themselves often move as the result of activity of several different muscle structures. This is particularly troubling for accelerometers as they cannot differentiate the gross movement of a bone lifting a passive muscle from the movement of the muscle itself actively changing position or shape.

For muscles that overly a flat bone structure, the skin and muscle will often slide over the bone due to unwanted forces. For example, activation of muscles in the cheek will cause detectable movement in the forehead. Accelerometers can account for such movement by employing acceleration detection in multiple axes to differentiate accelerations that are perpendicular to the bone from ones that are tangent to the bone. However, microphone-based systems will not only pickup the vibrations, pressure and sound of the muscle sliding over the bone, but due to the excellent vibration conduction properties of bone, the microphone may falsely interpret such signals as being generated by the muscle being monitored.

There exists a need for a device that will accurately detect changes in muscle thickness during contraction of a small muscle overlying a bone structure.

There further exists a need for a device that can determine if a muscle is contracting or relaxing.

SUMMARY OF THE INVENTION

In one example of the invention there is provided a device that will measure changes in muscle thickness of a small muscle overlying a bone structure, such as, but not limited to, the muscles of the hands, feet and face using a sensor with a compressible central structure and a rigid frame.

The device converts the changes in muscle thickness to an electrical signal using any method that can monitor the compressible central structure of the sensor. Such methods may operate on the principle of stretching, compressing, proximity sensing, sliding, differential gratings, or bending to sense the changes in muscle thickness of small muscles.

The device is optimally sized to fit the small muscle of interest. The device shall preferably have an area that is between 50% smaller to 75% larger than the active area of the muscle structure. The active area is that area of adjacent skin that will be displaced by muscle movement and can cause compression in the central structure of the sensor. This ensures that a majority of the muscle movement will be captured.

The shape of the device matches the approximate proportions of the muscle being monitored. It is expected that a short, fat muscle would be monitored with a sensor that has an aspect ratio approaching 1:1 while a long, thin muscle may have an aspect ratio that approaches as much as 4:1 The actual shape of the sensor may be rectangular in nature, but may also draw from any shape which reasonably fits the muscle to be monitored including polygons, ovoids, crescent and tear-drop shapes as well as general shapes that may contain a variety of curves and straight segments. Overall, any structure which can be expected to cover at least 50% of the active muscle area for the muscle of interest and for the population involved is acceptable.

The device has the ability to be temporarily attached to the skin overlying the small muscle. Such attachment will preferably be at the frame of the device, but could include belts, double-sided tape, or other methods of holding the sensor in reasonable contact with the body.

The rigid frame of the structure ensures that the device has a solid reference point on the surface of the body. The compressible central structure effectively allows a difference signal to be created between the rigid frame and the central structure which will ignore any movements generated outside of that area.

The rigid frame may be constructed of plastic and is only required to be more rigid than the compressible central structure. Therefore the rigid frame may in fact be a rubberized material. It is expected that a rigid structure where such structure has a Shore Hardness value that is at least 20 points higher than the central structure would be appropriate.

The compressible central structure may be composed of materials such as foam, rubber or cork. Such a compressible structure can also be attained by stretching flexible materials across a frame or by laminating film materials to a flexible substrate. In general, any structure which will allow mechanical motion relative to the rigid frame is acceptable. Once mechanical motion is present, such motion can be converted to an electrically compatible signal through methods of resistivity, piezo electric films, capacitive monitoring, optical sensing, load cells, polymer materials, linear differential transformers, magnetic detection, resonant tuning or other such methods well understood in the art.

In one example of the invention there is provided a muscle thickness sensor for detecting muscle movement over a bone structure. The muscle thickness sensor comprises a frame dimensioned for skin contact placement over a muscle of interest; muscle contraction sensing means within the frame comprising material adapted for elastic compressive deformation relative to the frame when said muscle of interest contracts; and, signal creation means for converting the elastic compressive deformation into a detectable electrical signal having a magnitude relative to the thickness of the muscle of interest.

The muscle of interest has a first relaxed state corresponding to a first muscle thickness and a first elastic compressive deformation of the sensing means and a second flexed state corresponding to a second muscle thickness and a second elastic compressive deformation of the sensing means. The first elastic compressive deformation is converted by the signal creation means into a first electrical signal and the second elastic compressive deformation is converted by the signal creation means into a second electrical signal. The first electrical signal and the second electrical signal are processed by processing means into a measurement of muscle thickness in the first relaxed state and the second flexed state respectively.

In the invention a displacement of adjacent bone structure causes no elastic compressive deformation of the muscle contraction sensing means resulting in the first and second electrical signals being noise free.

Flexure of the muscle of interest creates an adjacent active area of displacement of the covering skin so that the muscle thickness sensor is adapted for between 50% and 175% coverage of the active area for optimal muscle flexure detection.

In another example of the invention the frame is fabricated from a suitable resilient material such as a thermoplastic or a polymer material. However, the frame can be fabricated from suitable resilient material having a Shore Hardness value about 20 points greater than the Shore Hardness value of the muscle contraction sensing means.

In one example of the invention the muscle contraction sensing means has a Shore Hardness value of about 60.

In one example of the invention the signal creation means comprises strain sensitive materials that are one of capacitance sensitive, polarization sensitive, piezo-electric, magnetic sensitive.

In another example of the invention the muscle thickness sensor for detecting muscle movement over a bone structure comprises a frame dimensioned for skin contact placement over a muscle of interest. The frame has a skin contact side. The sensor further comprises a muscle contraction sensing membrane on the skin contact side adapted for elastic flexure when the muscle of interest contracts. The membrane is strain sensitive and adapted to convert elastic flexure into an electric signal having a magnitude relative to the thickness of the muscle of interest. Processing means are included to process the electrical signals into a measurement of muscle thickness in the first relaxed state and the second flexed state respectively.

OBJECTS AND ADVANTAGES OF THE INVENTION

It is an object of the invention to provide a muscle thickness sensor that is able to detect changes in muscle thickness during contraction of small muscles.

It is another object of the invention to provide a muscle thickness sensor that generates a signal that is relatively free of ambient noise from the movement of other body muscles and bone structures.

It is a further object of the invention to provide a muscle thickness sensor that is adaptable for various shapes of muscles.

It is yet a further object of the invention to provide a muscle thickness sensor that is able to differentiate between muscle contraction and relaxation.

Still further objects and advantages will become apparent from a consideration of the ensuring description and drawings.

DETAILED DESCRIPTION

Figure 1:
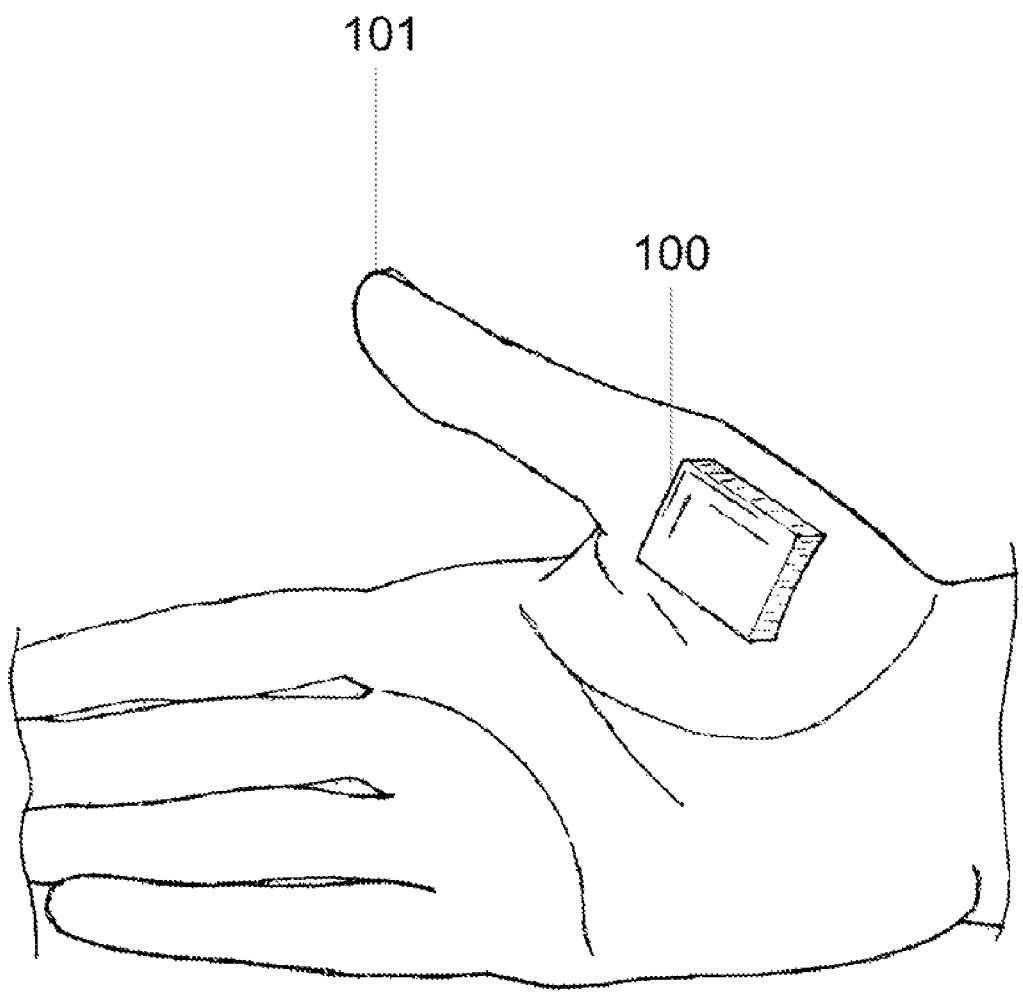
FIG. 1 is a diagram of one example of the invention laid over a small muscle in the thumb.

Referring to FIG. 1, the muscle thickness sensor (100) is shown in context, fixed to the skin above a small muscle overlying bone in the thumb (101). The sensor (100) is the approximate size of the active area of the muscle of interest, making it easy to apply and obtain measurements quickly. There is no need for repositioning and reattachment of the sensor because the muscle of interest will act on the majority of the compressible central structure of the sensor. The sensor (100) is depicted as rectangular but is not limited to that specific shape.

Figure 2:
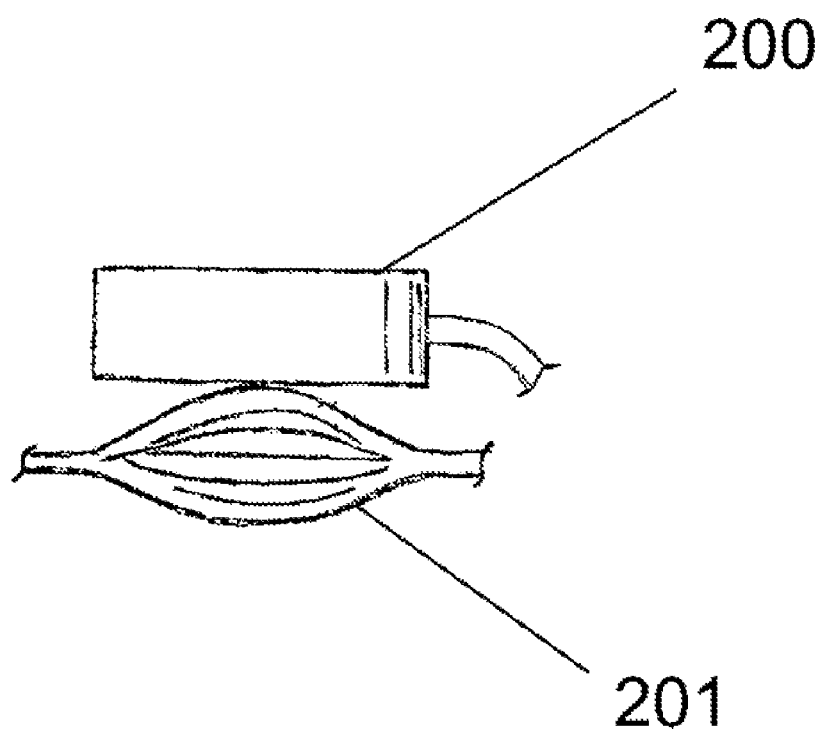
FIG. 2 is a diagram of a conventional microphone overlying a small, contracted muscle.

FIG. 2 shows the deficiency of a prior art sensor and in particular a conventional microphone (200). The microphone will detect changes in the muscle (201) based solely on the pressure waves (sound) from the muscle (201). However, the sound from such a muscle is not easily separated from the sound of other muscles, especially if such neighboring muscles are larger than the muscle of interest. In addition, the flat bottom surface of most microphones creates a large gap from the underlying muscle, causing the microphone to displace greatly when the muscle contracts and relaxes. This in turn causes air or liquid coupled microphones to lose the signal and the magnitude of such signals to vary greatly over time depending on the attachment methods used. Thus, this additional displacement decreases the accuracy of the conventional microphone.

Figure 3:
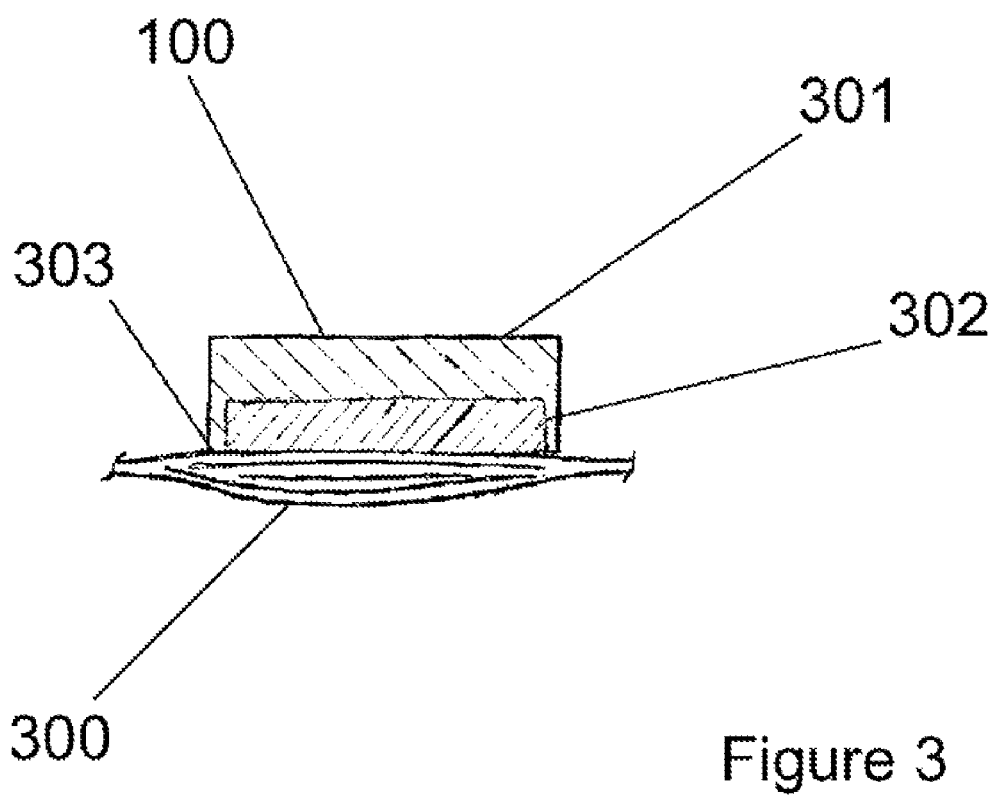
FIG. 3 is a diagram showing a cross-sectional view of one example of the device overlying a small, relaxed muscle.

FIG. 3 gives a more detailed diagram of the muscle thickness sensor (100), of the present invention shown as the approximate size of the underlying relaxed muscle (300). The cross-sectional view of the sensor (100) shows it consisting of a rigid frame (301), compressible central structure (302) and temporary skin attachment material (303). Belts and straps can also be used to ensure that the sensor remains in contact with the overlaying skin.

Figure 4:
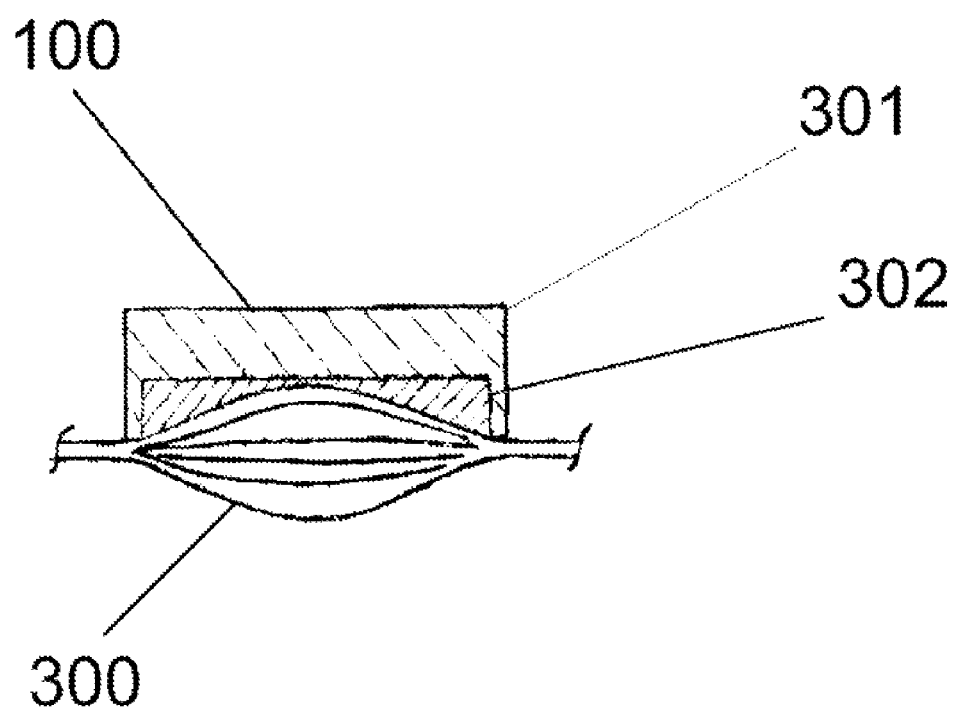
FIG. 4 is a diagram showing a cross-sectional view of one example of the device overlying a small, contracted muscle.

FIG. 4 shows the changes in the structure of the sensor (100) when the underlying small muscle (300) contracts. The relative size of the sensor (100) in comparison to the contracting small muscle (300), combined with the compressive nature of the central structure (302), enables the rigid frame (301) of the sensor (100) to stay in place while the muscle deforms the compressible central structure (302). The sensor (100) can then more accurately detect the difference between a contracted and a relaxed muscle through these changes in muscle thickness.

Figure 5:
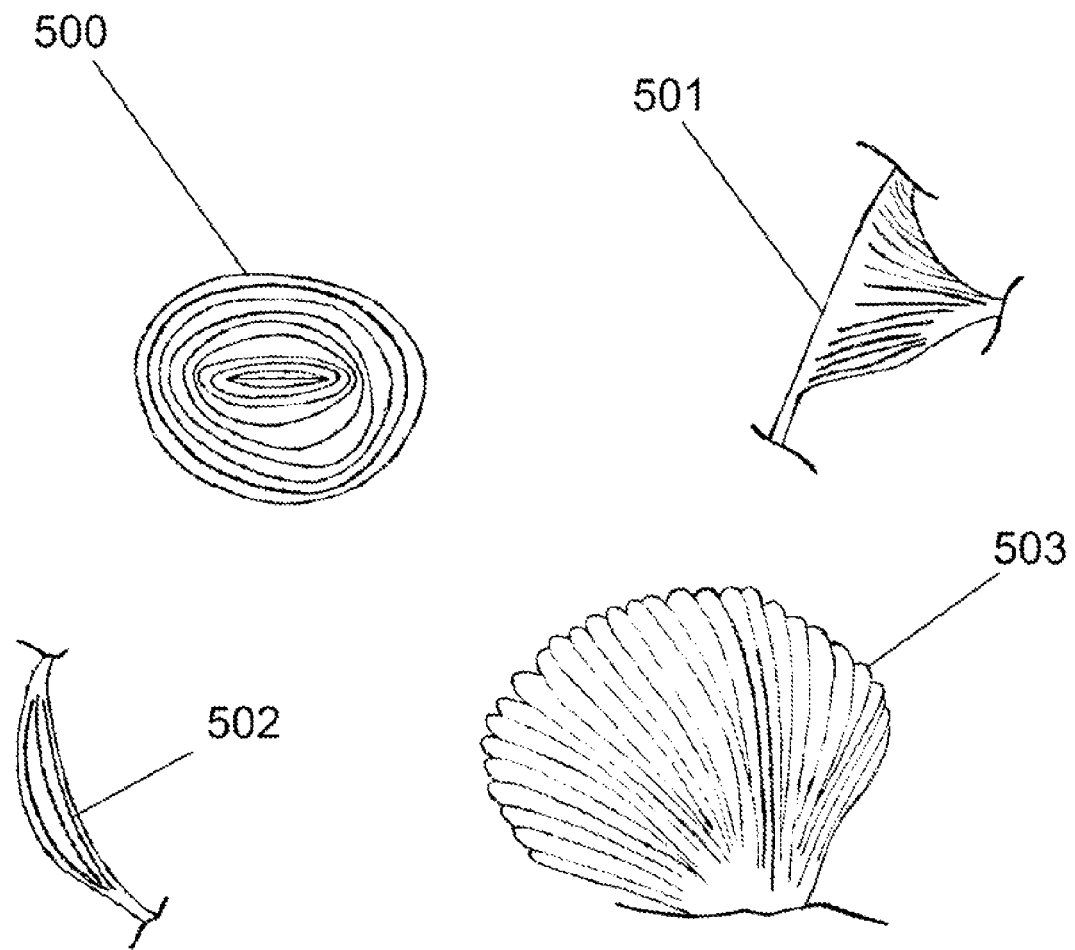
FIG. 5 is a diagram showing a variety of muscle shapes found in the body.

FIG. 5 gives a glimpse of the variety of shapes and sizes of small muscles found in the body: oval (500), triangular (501), crescent (502) and fan-shaped (503). There are many additional muscle shapes in the human body than that which is shown in FIG. 5, such as rectangular, tear-drop, and pie-shaped, and a greater variety of sizes than those of FIG. 5.

Figure 6:
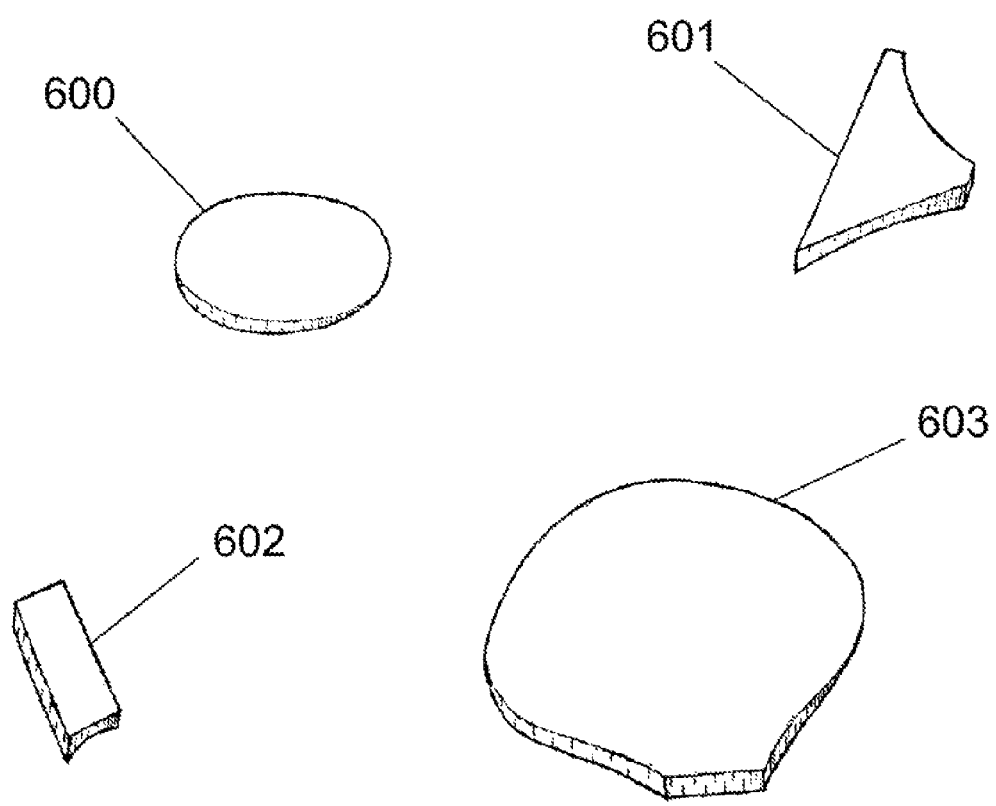
FIG. 6 is a diagram showing a variety of sensor shapes adapted to the muscles shown in FIG. 5.

FIG. 6 shows possible sensor adaptations to the muscles shown in FIG. 5: oval (600), triangular (601), rectangular (602) and fan-shaped (603). The range of muscle shapes shown in FIG. 5 highlights the necessity in having sensors of similar shapes so as to ensure acceptable coverage of the active area of the muscle of interest. Comparing FIGS. 5 and 6, the sensor would cover at least 50% of the active area of the corresponding muscle of interest.

Figure 7:
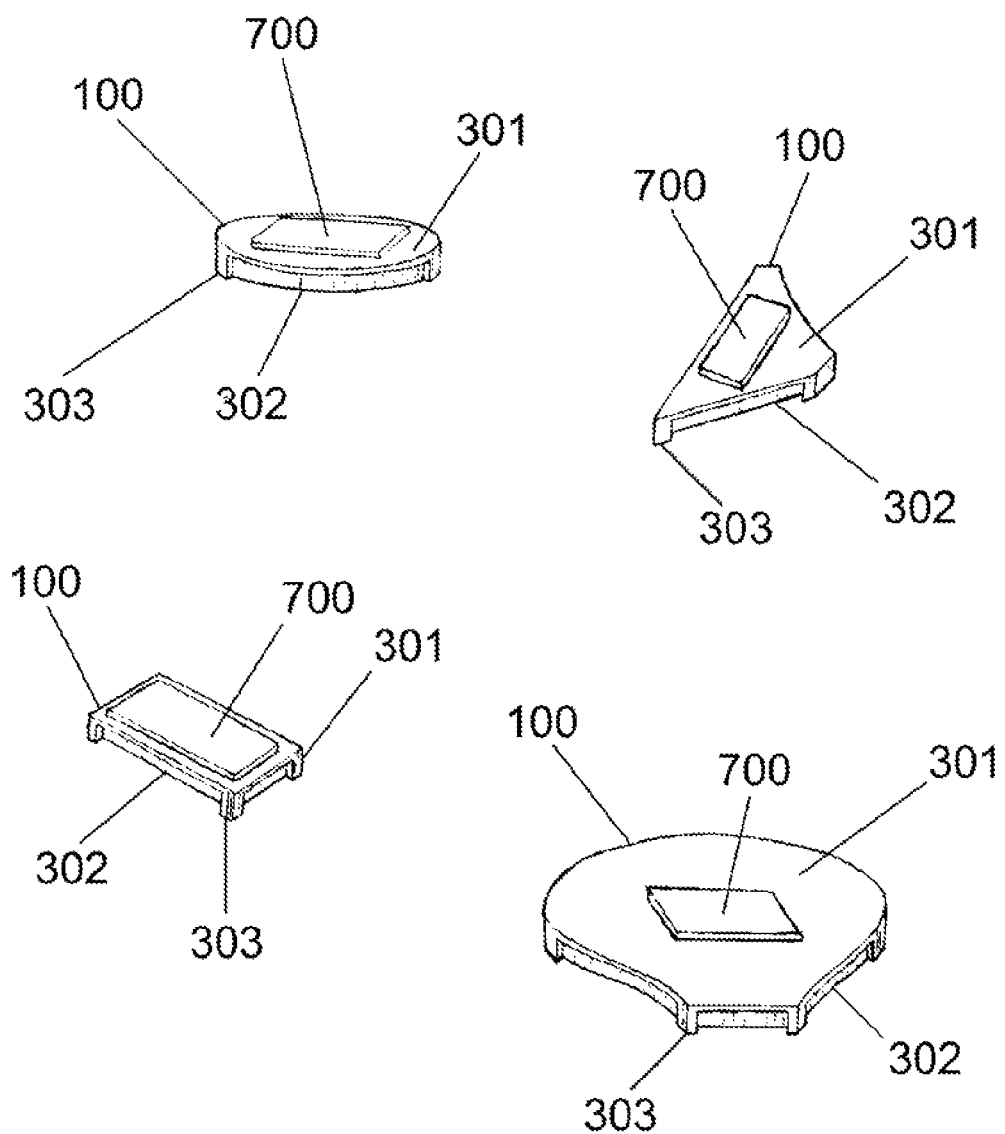
FIG. 7 is a diagram showing a variety of sensors comprising sensor frames and sensor compressible material having various shapes and adapted to fit different muscle shapes.

FIG. 7 details the device (100), in the present invention, in a variety of shapes adapted to the muscle shapes shown in FIG. 5. Processing means in the form of optional circuitry (700) is shown as attached to the rigid frame (301) for completeness. In the present invention, the circuitry would take in and transmit the electrical signal to a computer or other recording device. The rigid frame (301), compressible central structure (302) and temporary skin attachment material (303) are specific to each muscle shape while still using the same technique to measure muscle thickness. The similarity in shape and size of the sensor and the active area of the muscle of interest will allow for more accurate detection of the changes in muscle thickness and the difference between a contracting and relaxing muscle.

The present invention offers the following advantages over known muscle sensors as outlined below.

For small muscles, the rigid frame surrounding the majority of the muscle ensures movement of the muscle of interest is converted into a signal representative of the difference between the frame and the compressible central structure. The signal remains unaffected by movement from adjacent larger structures (muscles, bones, etc.). This effectively creates a "noiseless" signal from which extraneous signals need not be subtracted.

When the sensor of the present invention is applied to a muscle overlying a bone, the sensor's geometry permits the entire sensor to move with the movement of the bone without causing additional compression of the sensor's central structure and "noise". The signal recorded results only from movement of the muscle of interest.

When the sensor of the present invention is applied to a muscle overlying a flat bone structure any tangential movement of the skin and muscle over the bone will produce very little "noise" in the desired signal. Such "noise" will be due to irregularities in the bone surface similar in size to the muscle of interest.

The sensitivity of the sensor of the present invention permits the distinction between a muscle in a contracted state and a muscle in a relaxed state by measuring the thickness of the muscle in the two states.

Although the description above contains much specificity, these should not be construed as limiting the scope of the invention but as merely providing illustrations of the presently preferred embodiment of this invention. Thus the scope of the invention should be determined by the appended claims and their legal equivalents.

What is claimed is:

1. A muscle thickness sensor for detecting muscle thickness over a bone structure, said muscle thickness sensor comprising:
a rigid frame dimensioned for contact placement on a skin surface over a muscle of interest, said muscle of interest having a unique size and shape, wherein said rigid frame comprises a rigid top member having a top surface, a bottom surface, a size and a shape configurable to coincide with said unique size and shape of the muscle of interest and a plurality of supporting members for supporting said rigid top member off of said skin surface;
an elastic compressive deformation sensor disposed within said rigid frame and comprising an elastically compressible central structure comprising a top surface in contact with said rigid top member bottom surface and a bottom surface having contact with the skin surface, wherein a contraction of a muscle of interest is sensed by an elastic compressive deformation of said central structure within the rigid frame when said muscle of interest undergoes said contraction;
an electrical circuit disposed on said rigid top member top surface for converting said sensed elastic compressive deformation into a detectable electrical signal having a magnitude relative to the thickness of the muscle of interest; and,
a computer for receiving said detectable electrical signal and processing the detectable electrical signal into a measurement of muscle thickness.

2. The muscle thickness sensor of claim 1 wherein the muscle of interest has a first relaxed state corresponding to a first muscle thickness and a first elastic compressive deformation and a second flexed state corresponding to a second muscle thickness and a second elastic compressive deformation.

3. The muscle thickness sensor of claim 2 wherein said first elastic compressive deformation is converted by said electrical circuit into a first electrical signal and said second elastic compressive deformation is converted by the electrical circuit into a second electrical signal.

4. The muscle thickness sensor of claim 3 wherein said first electrical signal and said second electrical signal are processed by said computer into a measurement of muscle thickness in said first relaxed state and said second flexed state respectively.

5. The muscle thickness sensor of claim 4 wherein a displacement of said bone structure causes no elastic compressive deformation of the elastic compressive deformation sensor resulting in the first and second electrical signals being relatively free of ambient noise from the movement of said bone structure.

6. The muscle thickness sensor of claim 5 wherein the flexure of the muscle of interest creates an adjacent active area of displacement of the covering skin so that the muscle thickness sensor provides between 50% and 75% coverage of said active area for optimal muscle flexure detection.

7. The muscle thickness sensor of claim 6 wherein the frame is fabricated from a suitable resilient material having a first Shore Hardness value and wherein the elastic compressive deformation sensor has a second Shore Hardness value.

8. The muscle thickness sensor of claim 7 wherein said first Shore Hardness value is about 20 points greater than said second Shore Hardness value, and wherein the second Shore Hardness value is about 60.

9. The muscle thickness sensor of claim 1 wherein the elastically compressible central structure said comprises materials for generating said detectable electrical signal upon deformation.

10. The muscle thickness sensor of claim 9 wherein said materials are one of capacitance sensitive, polarization sensitive, piezo-electric, magnetic sensitive and a strain sensitive membrane.

* * * * *